US011833073B1

(12) United States Patent
Czaplewski et al.

(10) Patent No.: US 11,833,073 B1
(45) Date of Patent: Dec. 5, 2023

(54) DYNAMIC CONVEX OSTOMY BARRIER

(71) Applicant: Hollister Incorporated, Libertyville, IL (US)

(72) Inventors: Gregory J. Czaplewski, Bloomingdale, IL (US); Patrick C Tetzlaff, Caledonia, WI (US); Brian T. Leadingham, Pleasant Prairie, WI (US)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 18/261,310

(22) PCT Filed: Apr. 25, 2023

(86) PCT No.: PCT/US2023/066155
§ 371 (c)(1),
(2) Date: Jul. 13, 2023

Related U.S. Application Data

(60) Provisional application No. 63/354,441, filed on Jun. 22, 2022.

(51) Int. Cl.
*A61F 5/443* (2006.01)
*A61F 5/449* (2006.01)
*A61F 5/44* (2006.01)
*A61F 5/448* (2006.01)

(52) U.S. Cl.
CPC .............. *A61F 5/443* (2013.01); *A61F 5/449* (2013.01); *A61F 2005/4483* (2013.01)

(58) Field of Classification Search
CPC ... A61F 5/443; A61F 5/449; A61F 2005/4483
See application file for complete search history.

(56) References Cited

U.S. PATENT DOCUMENTS

| 2,563,597 | A | | 8/1951 | Friedman |
| 2,765,790 | A | | 10/1956 | Dickson |
| 3,039,465 | A | | 6/1962 | Berger |
| 4,592,750 | A | * | 6/1986 | Kay ..................... A61F 5/4407 604/277 |
| 6,527,755 | B1 | * | 3/2003 | Salama ................ A61F 2/0013 604/326 |

(Continued)

FOREIGN PATENT DOCUMENTS

| EP | 2185110 B1 | 7/2016 |
| WO | 9218074 A1 | 10/1992 |

(Continued)

OTHER PUBLICATIONS

International Search Report issued by ISA/EPO in connection with PCT/US2023/066155 dated Jun. 15, 2023.

(Continued)

*Primary Examiner* — Guy K Townsend
(74) *Attorney, Agent, or Firm* — Levenfeld Pearlstein, LLC

(57) ABSTRACT

A convex ostomy barrier assembly for attaching an ostomy appliance to a peristomal skin surrounding a stoma includes a skin barrier, an inlet opening defined in the skin barrier for receiving the stoma, and a convexity adjusting device. The convexity adjusting device includes a convex insert and an inflatable bladder, wherein the convex insert is configured to provide a convexity to the skin barrier and the inflatable bladder is configured to adjust at least one characteristic of the convexity.

23 Claims, 6 Drawing Sheets

(56) References Cited

U.S. PATENT DOCUMENTS

| | | | |
|---|---|---|---|
| 6,723,079 B2 | 4/2004 | Cline | |
| 7,001,367 B2 | 2/2006 | Arkinstall | |
| 7,087,041 B2 * | 8/2006 | von Dyck | A61F 5/445 |
| | | | 604/338 |
| 7,258,661 B2 | 8/2007 | Davies et al. | |
| 7,347,844 B2 | 3/2008 | Cline et al. | |
| 7,857,796 B2 | 12/2010 | Cline et al. | |
| 7,976,522 B2 | 7/2011 | Hansen et al. | |
| 8,092,437 B2 | 1/2012 | Cline | |
| 8,096,980 B2 | 1/2012 | Cline | |
| 8,217,221 B2 | 7/2012 | Davies et al. | |
| 8,460,259 B2 | 6/2013 | Tsai et al. | |
| 8,845,606 B2 | 9/2014 | Nguyen-Demary et al. | |
| 8,858,520 B2 | 10/2014 | Gregory | |
| 8,998,862 B2 | 4/2015 | Hanuka et al. | |
| 8,998,867 B2 | 4/2015 | Sabeti | |
| 9,498,371 B2 * | 11/2016 | Salama | A61F 5/445 |
| 9,517,157 B2 | 12/2016 | Hanuka et al. | |
| 9,883,964 B2 | 2/2018 | Hanuka et al. | |
| 10,045,877 B2 * | 8/2018 | Weig | A61F 5/445 |
| 10,864,107 B2 * | 12/2020 | Weig | A61F 5/445 |
| 11,020,265 B2 * | 6/2021 | Vila | A61F 5/443 |
| 11,166,838 B2 | 11/2021 | Cline et al. | |
| 2002/0077611 A1 * | 6/2002 | von Dyck | A61F 5/442 |
| | | | 604/332 |
| 2007/0088280 A1 * | 4/2007 | Gomez | A61M 25/04 |
| | | | 604/174 |
| 2011/0092929 A1 * | 4/2011 | Weig | A61F 5/445 |
| | | | 604/338 |
| 2013/0047993 A1 | 2/2013 | Lally | |
| 2018/0318126 A1 * | 11/2018 | Weig | A61F 5/445 |
| 2019/0133813 A1 | 5/2019 | Cline et al. | |
| 2019/0231580 A1 * | 8/2019 | Czaplewski | A61F 5/445 |
| 2020/0253777 A1 * | 8/2020 | Jones | A61F 5/443 |
| 2020/0337885 A1 * | 10/2020 | Donovan | A61F 5/443 |
| 2021/0085510 A1 * | 3/2021 | Langhorn | A61F 5/443 |
| 2022/0168131 A1 * | 6/2022 | Heckler | A61F 5/443 |

FOREIGN PATENT DOCUMENTS

| | | |
|---|---|---|
| WO | 2011091481 A1 | 8/2011 |
| WO | 2020220025 A1 | 10/2020 |

OTHER PUBLICATIONS

Written Opinion issued by ISA/EPO in connection with PCT/US2023/066155 dated Jun. 15, 2023.

* cited by examiner

DYNAMIC CONVEX OSTOMY BARRIER

This is a 371 National Stage Application of International Application No. PCT/US2023/066155, filed Apr. 25, 2023, which claims the benefit of and priority to U.S. Provisional Application No. 63/354,441, filed Jun. 22, 2022, the entireties of which are incorporated fully herein by references.

BACKGROUND

This disclosure is related to a convex ostomy barrier. More particularly, the present disclosure pertains to an ostomy barrier appliance having a localized adjustable convexity feature.

Ostomy pouches for collecting bodily waste are used by individuals who have had surgery such as a colostomy, ileostomy, or urostomy. An ostomy pouch may be attached to a user via an ostomy barrier, which is configured to seal against peristomal skin surfaces and protect the peristomal surfaces from exposure to stomal effluent. However, the topography of stomas and peristomal surfaces surrounding stomas varies among patients, and sealing an ostomy appliance against such different peristomal surfaces and stomas remain as an area for further improvements. For example, a stoma may protrude more or less, or may even be flush or recessed.

A person with an ostomy having a stoma that is flush or recessed may find that applying external support or pressure from a barrier in the peristomal region aids in directing the discharge of effluent from the stoma directly into the ostomy pouch. Accordingly, the effectiveness of an adhesive seal between the ostomy barrier and the peristomal skin surface (i.e., a seal formed by the adhesive layer) may be prolonged. Thus, convex inserts and convex ostomy barriers, such as ADAPT® convex barrier rings available through the Applicant of the present application, have been developed to apply pressure around such peristomal regions.

However, the convexity of a conventional convex ostomy barrier or insert is fixed and may not work efficiently for all ostomates. Thus, convex ostomy barriers and convex inserts of various convexity depths have been made available in the market. Further, US 2019/0231580, which is assigned to the Applicant of the present application and incorporated herein by reference, discloses ostomy barrier appliances including a convexity adjusting device, which is configured to allow a user to provide a convexity to a generally flat skin barrier.

Accordingly, it is desirable to provide an improved ostomy barrier appliance that allows local adjustment of various characteristics of the barrier convexity according to the topography of user's stoma and peristomal surface.

BRIEF SUMMARY

A convexity adjusting device for an ostomy skin barrier configured to adjust a convexity of a skin barrier is provided according to various embodiments.

In one aspect, a convex ostomy barrier assembly for attaching an ostomy appliance to a peristomal skin surrounding a stoma may include a skin barrier, an inlet opening defined in the skin barrier for receiving the stoma, and a convexity adjusting device. The convexity adjusting device may include a convex insert and an inflatable bladder, wherein the convex insert may be configured to provide a convexity to the skin barrier, and the inflatable bladder may be configured to adjust at least one characteristic of the convexity.

In an embodiment, the inflatable bladder may be compartmentalized into a plurality of bladders, wherein the convexity adjusting device may be configured such that each of the plurality of bladders can be inflated or deflate separately. The convex insert may include a base and an upper layer. The upper layer may extend from the base to an inner periphery, and the inflatable bladder may be arranged adjacent a distal surface of the upper layer between the base and the upper layer. In such an embodiment, the inflatable bladder may be configured to provide a localized adjustment of a compressibility and/or a depth of the convexity by inflating or deflating one or more of the plurality of bladders.

In an embodiment, the ostomy barrier assembly may be provided with each of the plurality of bladders inflated to provide a generally uniform first compressibility around the convexity. In such an embodiment, one or more of the plurality of bladders may be deflated to adjust the first compressibility to a second compressibility at one or more of the corresponding locations to provide a localized and customized adjustment of the compressibility of the convexity, wherein the first compressibility is greater than the second compressibility. In another embodiment, the ostomy barrier assembly may be provided with each of the plurality of bladders deflated to provide a generally uniform third compressibility around the convexity. In such an embodiment, one or more of the plurality of bladders may be inflated to adjust the third compressibility to a fourth compressibility at one or more of the corresponding locations to provide a localized and customized adjustment of the compressibility of the convexity, wherein the third compressibility is less than the fourth compressibility.

In an embodiment, the inflatable bladder may be arranged between the convex insert and the skin barrier, wherein each of the plurality of bladders may be configured to be inflated or deflated separately to provide a localized and customized adjustment of a slope of the convexity. In such an embodiment, the inflatable bladder may be arranged in a concave portion of the convex insert. One or more of the plurality of bladders may be inflated to decrease the slope of the convexity at one or more the corresponding locations or deflated to increase the slope of the convexity at one or more the corresponding locations.

In an embodiment, the convex ostomy barrier assembly may be provided with each of the plurality of bladders filled with air to provide a generally uniform slope around the convexity, wherein one or more of the plurality of bladders may be compressed or popped to increase the slope of the convexity at one or more the corresponding locations.

In an embodiment, the inflatable bladder may be arranged between the convex insert and the skin barrier in a dome area and configured to adjust a depth of the convexity. In such an embodiment, the convex barrier assembly may be provided with the inflatable bladder substantially deflated to provide a first depth, wherein the inflatable bladder may be configured to be inflated by a user to increase the depth to a second depth, wherein the second depth is greater than the first depth. Alternatively, the convex barrier assembly may be provided with the inflatable bladder inflated to provide a third depth, wherein the inflatable bladder may be configured to be deflated by a user to decrease the depth to a fourth depth, wherein the fourth depth is less than the third depth.

In an embodiment, the inflatable bladder may be arranged between the convex insert and the skin barrier in a concave portion of the convex insert and configured to adjust a slope of the convexity. In such an embodiment, the convex barrier assembly may be provided with the inflatable bladder substantially deflated to provide a first slope, wherein the inflatable bladder may be configured to be inflated by a user to decrease the slope to a second slope, wherein the second slope is less than the first slope. Alternatively, the convex barrier assembly may be provided with the inflatable bladder inflated to provide a third slope, wherein the inflatable bladder may be configured to be deflated by a user to increase the slope to a fourth slope, wherein the fourth slope is greater than the third slope.

In an embodiment, the inflatable bladder may be arranged adjacent a distal surface of the convex insert and configured to adjust a compressibility of the convexity. The convex ostomy barrier assembly may be configured such that the compressibility of the convexity can be adjusted by inflating or deflating the inflatable bladder while a depth and a slope of the convexity defined by the convex insert remain unchanged. For example, the inflatable bladder may be configured to be inflated to increase the compressibility of the convexity and deflated to decrease the compressibility of the convexity. In such an embodiment, the inflatable bladder may be arranged proximate a base area of the convex insert.

In any of the foregoing embodiments, the convex ostomy barrier assembly may include a fluid inlet and a fluid path connecting the fluid inlet to the inflatable bladder, wherein the fluid inlet and the fluid path may provide a path for a fluid to enter or exit the inflatable bladder. The inflatable bladder may be configured to be inflated by inserting a fluid into the inflatable bladder and deflated by releasing the fluid from the inflatable bladder. The fluid may be air.

The foregoing general description and the following detailed description are examples only and are not restrictive of the present disclosure.

BRIEF DESCRIPTION OF THE DRAWINGS

The benefits and advantages of the present embodiments will become more readily apparent to those of ordinary skill in the relevant art after reviewing the following detailed description and accompanying drawings, wherein.

DETAILED DESCRIPTION

Figure 1:
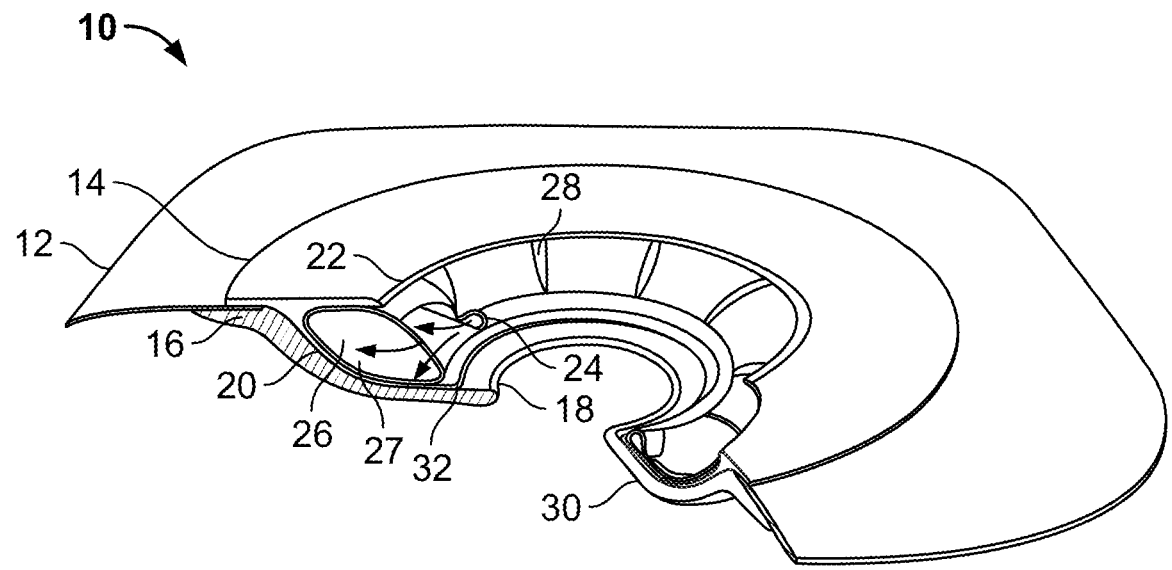
FIG. 1 is a perspective distal side view of an ostomy barrier appliance including a convexity adjusting device comprising a plurality of bladders for localized and customized adjustment of a compressibility and/or depth of a convexity according to an embodiment with a portion removed to illustrate its layered structure.

While the present disclosure is susceptible of embodiment in various forms, there is shown in the drawings and will hereinafter be described presently preferred embodiments with the understanding that the present disclosure is to be considered an exemplification and is not intended to limit the disclosure to the specific embodiments illustrated. The words "a" or "an" are to be taken to include both the singular and the plural. Conversely, any reference to plural items shall, where appropriate, include the singular.

Figure 7:
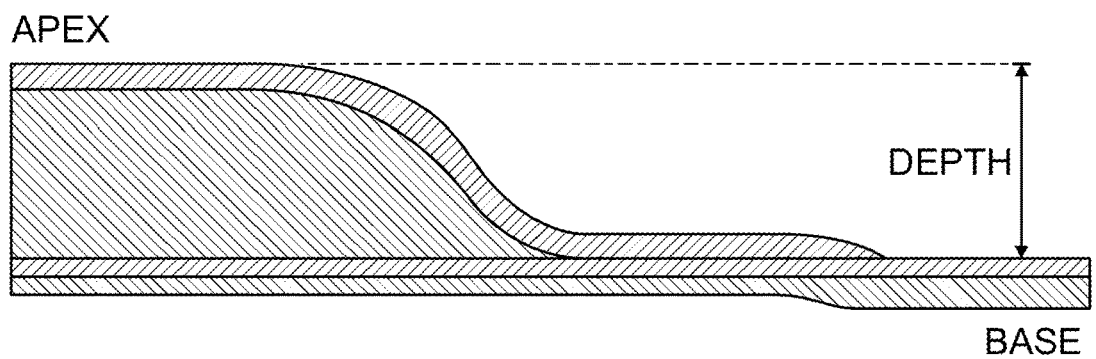
FIG. 7 is an illustration of a depth of a convex skin barrier.

The characteristics of convexity of a skin barrier can include depth, compressibility, flexibility, tension location, and slope. See, McNichol, L., Cobb, T., Depaifve, Y., Quigley, M., Smitka, K., & Gray, M., Characteristics of Convex Skin Barriers and Clinical Application: Results of an International Consensus Panel, J Wound Ostomy Continence Nurs., (2021) 48(6), 524-532, Abstract. The depth of a convex skin barrier is defined as a distance from the apex of the dome to the base of the skin barrier. Id, at pg. 526. The depth D can be measured as a magnitude of the convexity from the base lying on the peristomal skin to the highest point of the skin barrier as shown in FIG. 7. Id. Individual user's peristomal condition, such as depths of creases and folds around the stoma, should be carefully considered when determining a depth of a convex skin barrier to provide an optimal seal around the peristomal skin. Id.

Figure 8:
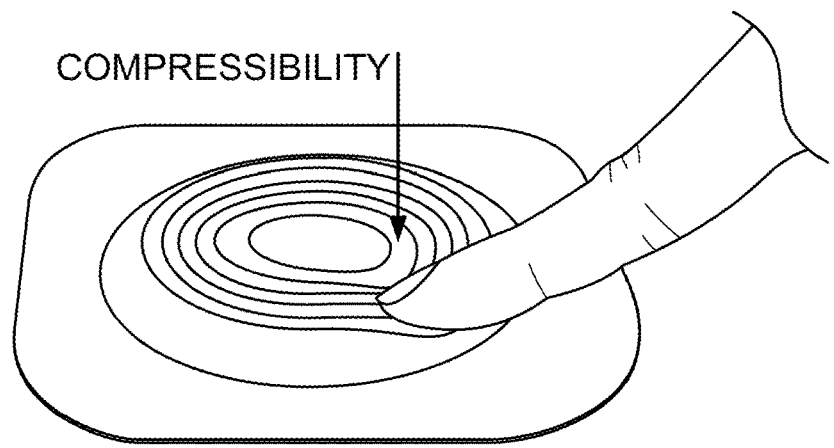
FIG. 8 is an illustration of compressibility of a convex skin barrier.

The compressibility of a convex skin barrier is defined as a capacity of the convex dome to be displaced or flattened as illustrated in FIG. 8. Id, at pg. 528. The compressibility may be measured as a force required to displace or flattened the dome portion of a convex skin barrier by a predetermined distance. A relatively easily compressible soft convex barrier may conform better to users with postoperative edema and/or a relatively firm abdomen. Id. A relatively less compressible firm convex barrier may apply more pressure on the peristomal skin to provide support needed for users with a relatively soft abdominal tone and/or creases around the stoma. Id.

Figure 9:
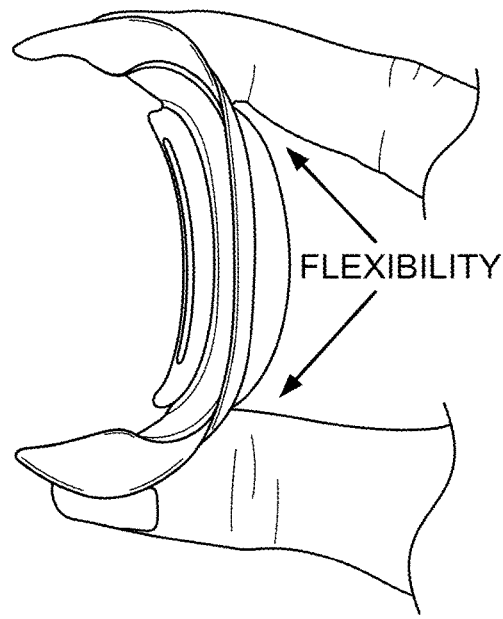
FIG. 9 is an illustration of flexibility of a convex skin barrier.

The flexibility of a convex skin barrier is defined as how easily the convex skin barrier can bend as illustrated in FIG. 9. Id, at pg. 529. The flexibility is an important characteristic to consider when a skin barrier needs to bend to conform to abdominal contours. Id. A relatively more flexible convex skin barrier may work well for users with multiple creases around stoma due to loose skin. Id.

Figure 10A:
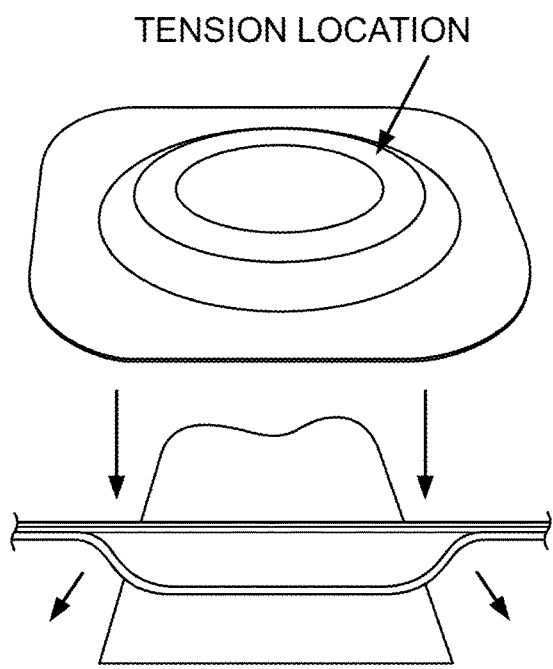
FIGS. 10A and 10B are illustrations of tension locations of a convex skin barrier.
Figure 10B:
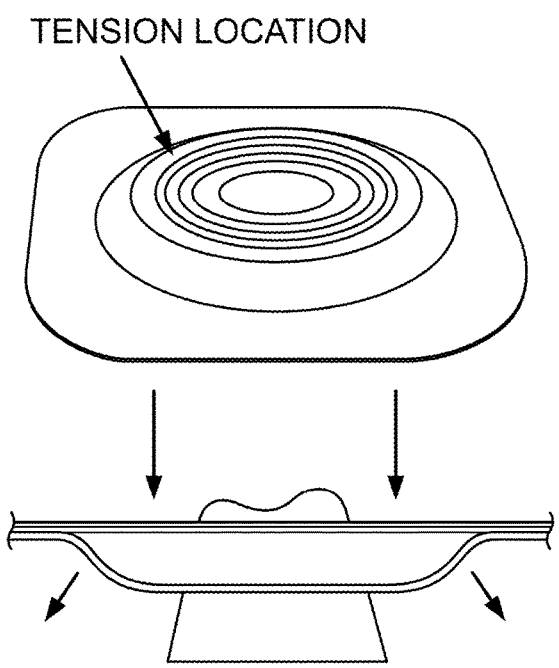

The tension location of a convex skin barrier is defined as the position in which a convex dome exerts downward and outward forces on the peristomal topography as illustrated in FIGS. 10A and 10B. Id, at pg. 530. A convex skin barrier configured to apply a tension close to a stoma may provide a consistent and reliable seal around the stoma that is flush to the skin or retraced below the skin. Id. For users with creases and folds around the stoma, a convex barrier skin barrier configured to apply a tension away from the stoma may help flatten the peristomal skin to provide a good seal. Id.

Figure 11:
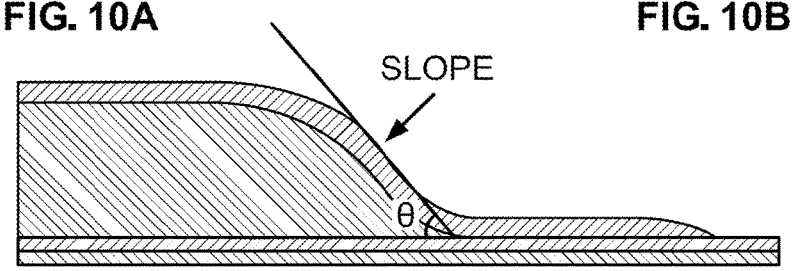
FIG. 11 is an illustration of a slope of a convex skin barrier.

The slope of a convex skin barrier is defined as an angle from the base of the dome to a periphery of the apex of the dome, as illustrated in FIG. 11. Id, at pg. 53. Creases and folds around the stoma can compromise a seal between a skin barrier and the skin. Adjusting the slope of a convex skin barrier according to user's peristomal topography can improve the seal. For example, a convex skin barrier with a relatively small slope and wider plateau may help flatten the peristomal skin creases and folds to achieve a good seal. Id.

Customizing and adjusting the depth, compressibility, flexibility, tension location, and/or slope of a convex skin barrier according to user's peristomal topography can provide an optimal seal around the stoma. The present disclosure provides an ostomy barrier appliance, including a convexity adjusting device configured to adjust one or more of the convexity characteristics of a skin barrier according to various embodiments.

Referring now to the figures, FIGS. 1-6 show an ostomy barrier appliance according to several embodiments. FIG. 1 is a perspective view of the ostomy barrier appliance 10 according to an embodiment with a portion removed and viewed from a pouch-facing side (also referred to herein as a distal side) to illustrate a layered construction of the ostomy barrier appliance 10. The ostomy barrier appliance 10 may generally include a tape 12, a skin barrier 16, a convexity adjusting device 14, and an inlet opening 18 for receiving a stoma (not shown). The convexity adjusting device 14 may include an inflatable adjusting member 26 configured to adjust at least one characteristic of the convexity of the ostomy barrier appliance 10.

The tape 12 may include a first adhesive layer and a first backing layer. The first adhesive layer of the tape 12 may be formed from a suitable medical adhesive, such as an acrylic adhesive. The first backing layer may be formed from a suitable material, such as a nonwoven material or a thin polymeric film. In another embodiment, the tape 12 may comprise a hydrocolloid adhesive and a film backing layer.

In some embodiments, the skin barrier 16 may include a second backing layer laminated on the pouch-side surface of the skin barrier 16. The second backing layer may be formed from a suitable heat sealable polymeric material, such that the backing layer may be heat sealed to the tape 12. The skin barrier 16 may be formed from a suitable skin-contact adhesive, such as hydrocolloid adhesives.

In an embodiment, the convexity adjusting device 14 may be formed as a convex insert 14 comprising a base 22, an upper layer 20, and an inflatable adjusting member 26. The convex insert 14 may be configured to define and support a convexity of the skin barrier 16. The upper layer 20 may extend from the base 22 to an inner periphery 32, and the inflatable bladder 26 may be arranged adjacent a distal surface (pouch side surface) of the upper layer 20 between the base 22 and the upper layer 20.

In the embodiment of FIG. 1, the inflatable bladder 26 may be compartmentalized into a plurality of bladders 27, wherein each of the plurality of bladders may be separately inflated or deflated to provide localized adjustment of a compressibility and/or depth of the convexity of the ostomy barrier appliance 10. Each of the plurality of bladders 27 may be separated from adjacent bladders by a sealed section 28 and may be inflated through a vessel 24.

In an embodiment, the ostomy barrier appliance 10 may be configured as a convex ostomy barrier including a dome 30 supported by the convex insert 14 including the inflatable bladder 26, where each of the plurality of bladders 27 may be inflated to provide a generally uniform initial compressibility and depth around the dome 30. In use, a user may deflate one or more of the plurality of bladders 27 according to user's peristomal topography to decrease the compressibility and/or depth in desired areas to create a seal that best fits user's need. Alternatively, the ostomy barrier appliance 10 may be provided each of the plurality of bladders 27 deflated or mostly deflated, and a user may inflate one or more of the plurality of bladders 27 to increase the compressibility and/or depth in desired areas. A user may inflate or deflate one or more of the plurality of bladder 27 by inserting or releasing a fluid, such as air, in a controlled amount to achieve the desired compressibility and/or depth.

FIGS. 2-6 show an ostomy barrier appliance 110, 210, 310, 410 according to several embodiments. The ostomy barrier appliance 110, 210, 310, 410, may be configured similar to ostomy barrier appliance 10 of FIG. 1, and may generally include a tape 12, a skin barrier 16, a convexity adjusting device 114, 314, 414, 414, and an inlet opening 18 for receiving a stoma. The convexity adjusting device 114, 214, 314 may include an inflatable bladder 126, 226, 326 which may be configured to adjust at least one characteristic of the convexity of the ostomy barrier appliance 110, 210, 310.

Figure 2:
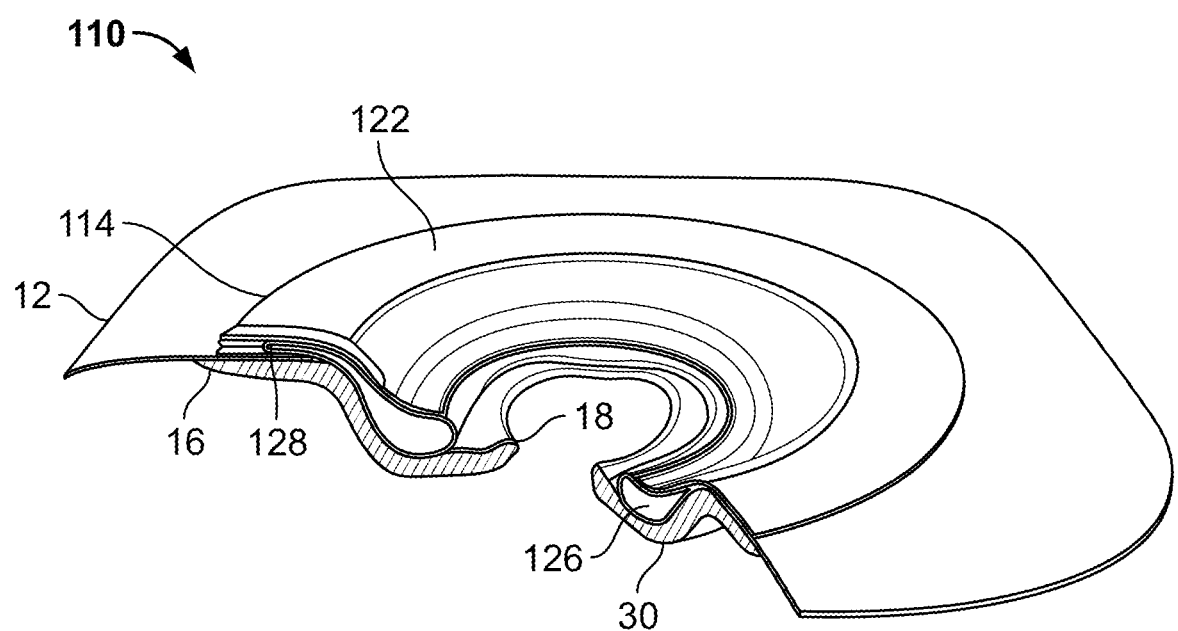
FIG. 2 is a perspective distal side view of an ostomy barrier appliance including a convexity adjusting device comprising an inflatable bladder for customized adjustment of a convexity depth according to an embodiment with a portion removed to illustrate its layered structure.
Figure 3A:
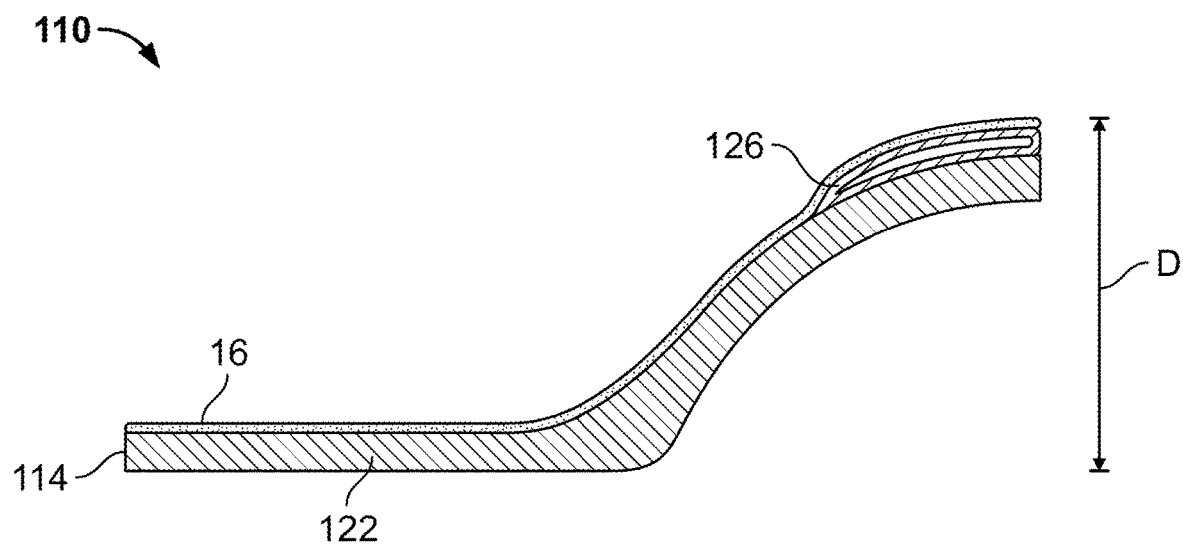
FIG. 3A is a schematic cross-section view of the convexity adjusting device of FIG. 2 with a deflated bladder.
Figure 3B:
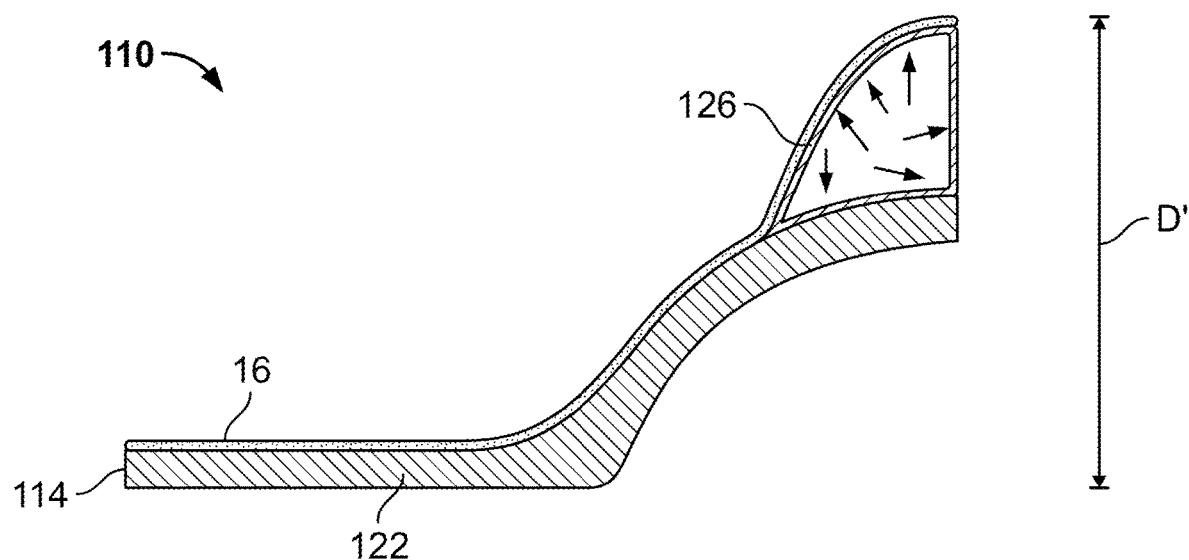
FIG. 3B is a schematic cross-section view of the convexity adjusting device of FIG. 2 with an inflated bladder.

FIG. 2 is a perspective view of an ostomy barrier appliance 110 according to an embodiment. The ostomy barrier appliance 110 may include a convexity adjusting device 114 comprising a convex insert 122 and an inflatable bladder 126. In this embodiment, the inflatable bladder 126 may be arranged between the convex insert 122 and the skin barrier 16 in a dome area 30 and configured to adjust a convexity depth of the skin barrier 16. In an embodiment, the ostomy barrier appliance 110 may comprise a fluid path 128 configured to allow a fluid, such as air, to enter and exit the inflatable bladder 26. FIG. 3A illustrates the inflatable bladder 126 substantially deflated, wherein the depth D of the convexity of the ostomy barrier appliance 110 is substantially defined by the depth of the convex insert 122. FIG. 3B illustrates the inflatable bladder 126 inflated to increase the depth D' of the convexity, wherein the depth D' at an inflated state is greater than the depth D at a deflated state. The inflatable bladder 26 may be configured to be inflated or deflated by inserting or releasing an amount of fluid to provide a desired depth of the convexity of the ostomy barrier appliance 110.

Figure 4A:
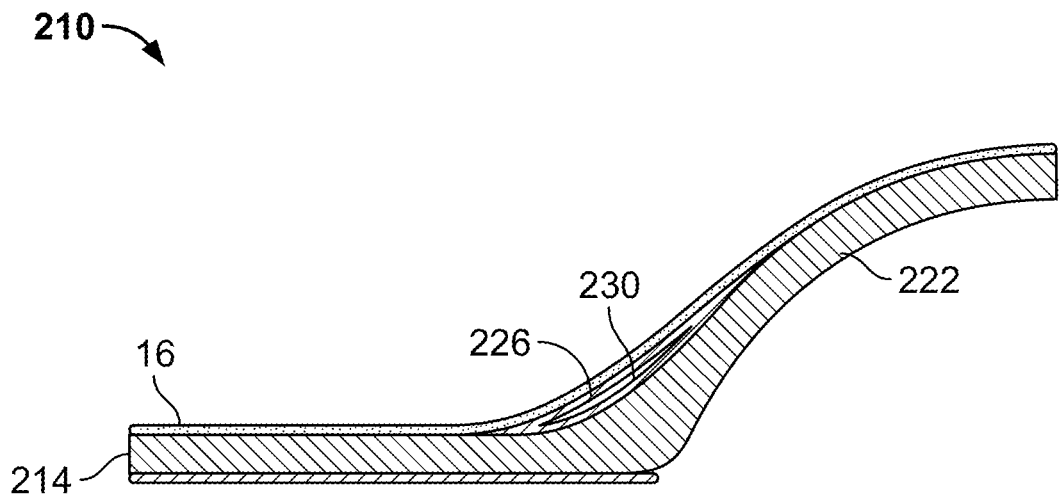
FIG. 4A is a schematic cross-section view of a convexity adjusting device comprising an inflatable bladder for customized adjustment of a convexity slope according to another embodiment, wherein the inflatable bladder is deflated.
Figure 4B:
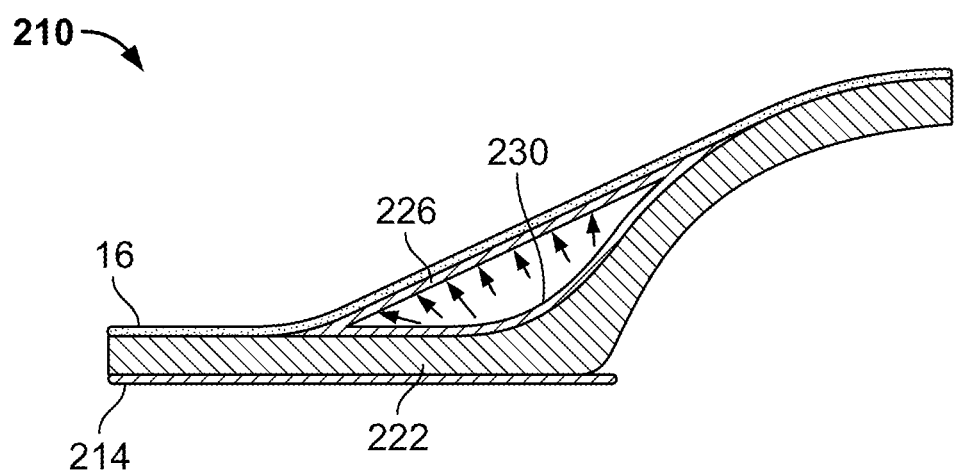
FIG. 4B is a schematic cross-section view of the convexity adjusting device of FIG. 4A with the inflatable bladder inflated.

FIGS. 4A and 4B are cross-sectional views of an ostomy barrier appliance 210 according to another embodiment. Similar to the convex adjusting device 114, a convexity adjusting device 214 may comprise a convex insert 222 and an inflatable bladder 226. In this embodiment, the inflatable bladder 226 may be arranged between the convex insert 222 and the skin barrier 16 in a concave area 230 of the convex insert 222 and configured to adjust a convexity slope of the skin barrier 16. In FIG. 4A, the inflatable bladder 226 may be substantially deflated, wherein the convexity of the ostomy barrier appliance 210 including the slope is substantially defined by the convexity of the convex insert 222. In FIG. 4B, the inflatable bladder 226 is inflated to decrease the slope. As shown, the slope of the convex barrier appliance 210 is smaller or shallower when the inflatable bladder 226 is inflated (FIG. 4B) than when the inflatable bladder 226 is deflated (FIG. 4A). The inflatable bladder 226 may be configured to be inflated or deflated by inserting or releasing an amount of fluid, such as air, to provide a desired slope of the convexity of the ostomy barrier appliance 210.

Figure 5A:
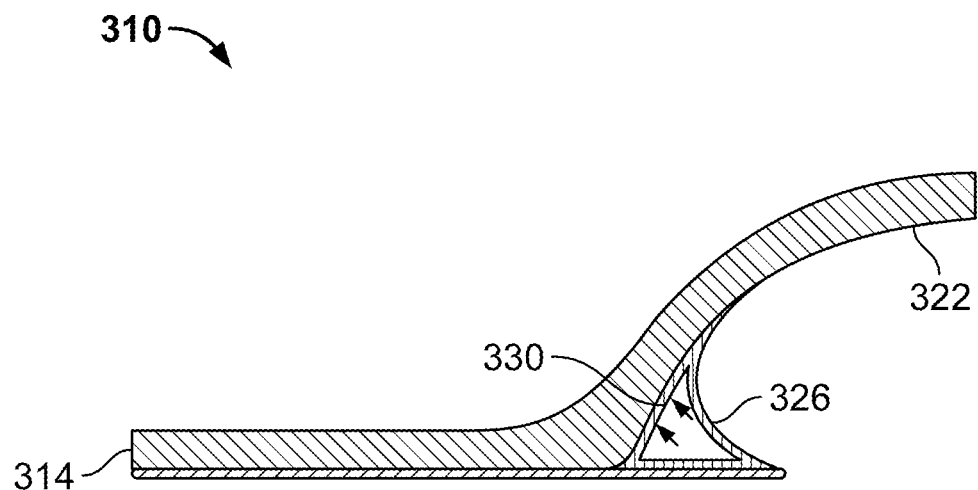
FIG. 5A is a schematic cross-section view of a convexity adjusting device comprising an inflatable bladder for customized adjustment of a compressibility according to yet another embodiment with the inflatable bladder deflated.
Figure 5B:
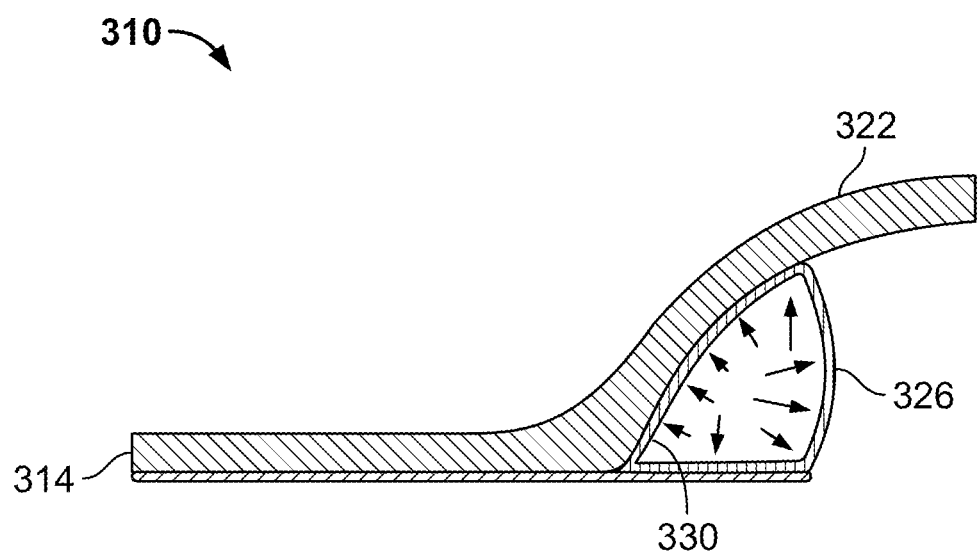
FIG. 5B is a schematic cross-section view of the convexity adjusting device of FIG. 5A with the inflatable bladder inflated.

FIGS. 5A and 5B are cross-sectional views of an ostomy barrier appliance 310 according to an embodiment. Similar to the convex adjusting device 114, 214, a convexity adjusting device 314 may comprise a convex insert 322 and an inflatable bladder 326. In this embodiment, the inflatable bladder 326 may be arranged adjacent a distal surface (pouch side surface) of the convex insert 322 proximate a base area 330 and configured to adjust a compressibility of the convexity of the skin barrier 16. In an embodiment, the ostomy barrier appliance 310 may be configured such that the compressibility may be adjusted by inflating or deflating the inflatable bladder 326 while the depth and slope of the convexity defined by the convex insert 322 may remain unchanged. In another embodiment, the ostomy barrier appliance 310 may be configured such that the compressibility, depth and/or slope of the convexity defined by the convex insert 322 may be adjusted by inflating or deflating the inflatable bladder 326. In FIG. 5A, the inflatable bladder 326 may be substantially deflated such that the compressibility of ostomy barrier appliance 310 may be substantially defined by the compressibility of the convex insert 322. In FIG. 5B, the inflatable bladder 326 may be inflated to increase the compressibility of the ostomy barrier appliance 310. The compressibility of the ostomy barrier appliance 310 when the inflatable bladder 326 is inflated may be greater or firmer when compared to when the inflatable bladder 326 is deflated. The inflatable bladder 326 may be configured to be inflated or deflated by inserting or releasing an amount of fluid, such as air, to provide a desired compressibility of the convexity of the ostomy barrier appliance 310.

Figure 6:
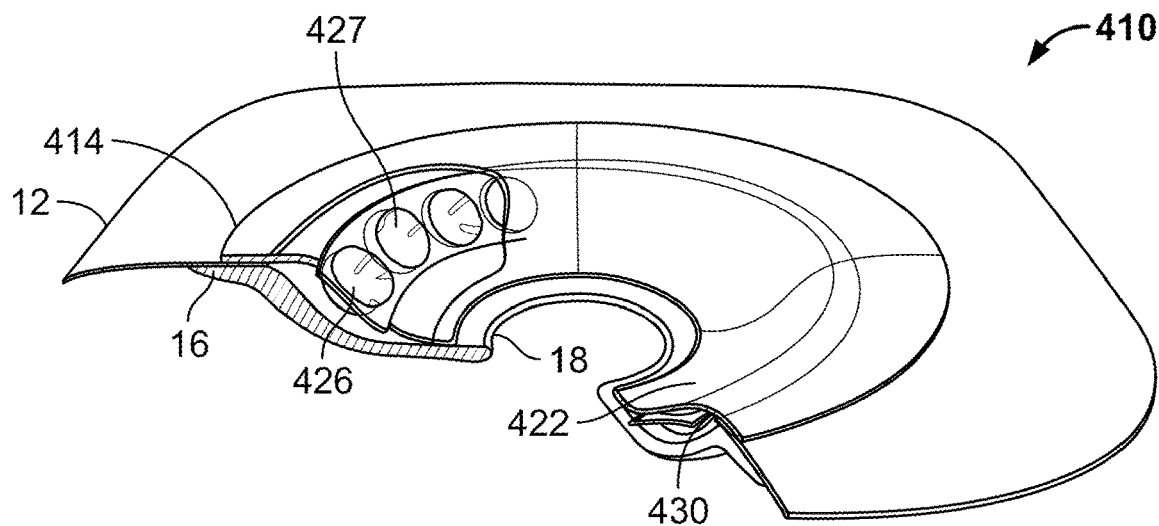
FIG. 6 is a perspective distal side view of an ostomy barrier appliance including a convexity adjusting device comprising a plurality of bladders for localized and customized adjustment of a convexity slope according to an embodiment with a portion removed to illustrate its layered structure.

FIG. 6 is a perspective view of an ostomy barrier appliance 410 according to an embodiment with a portion removed and viewed from a distal side. The ostomy barrier appliance 410 may be configured similar to the ostomy barrier appliance 210 comprising a convexity adjusting device 414 that includes a convex insert 422 and an inflatable bladder 426. The inflatable bladder 426 may be arranged between the convex insert 422 and the skin barrier 16 generally in a middle portion or in a concave portion 430 of the convex insert 422 and configured to adjust a convexity slope of the skin barrier 16. In this embodiment, the inflatable bladder 426 may include a plurality of bladders 427, each of which may be separately inflated or deflated to provide a localized adjustment of the convexity slope. In use, a user may inflate one or more of the plurality of bladders 427 to decrease the convexity slope or deflate one or more of the plurality of bladders 427 to increase the convexity slope at desired locations. In an embodiment, the inflatable bladder 426 may comprise a plurality of pockets 427 filled with air. In use, a user may compress or pop one or more of the plurality of air pockets 427 to increase the convexity slope at desired locations around the ostomy barrier appliance 410.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A convex ostomy barrier assembly for attaching an ostomy appliance to a peristomal skin surrounding a stoma, comprising:
   a skin barrier comprising an adhesive;
   an inlet opening defined in the skin barrier for receiving the stoma; and
   a convexity adjusting device comprising a convex insert and an inflatable bladder;
   wherein the convex insert is configured to provide a convexity to the skin barrier, and wherein the inflatable bladder is configured to adjust at least one characteristic of the convexity.

2. The convex ostomy barrier assembly of claim 1, wherein the inflatable bladder is compartmentalized into a plurality of bladders, wherein the convexity adjusting device is configured such that each of the plurality of bladders can be inflated or deflate separately.

3. The convex ostomy barrier assembly of claim 2, wherein the convex insert includes a base and an upper layer, wherein the upper layer extends from the base to an inner periphery and the inflatable bladder is arranged adjacent a distal surface of the upper layer between the base and the upper layer, wherein the inflatable bladder is configured to provide a localized adjustment of a compressibility and/or a depth of the convexity by inflating or deflating one or more of the plurality of bladders.

4. The convex ostomy barrier assembly of claim 2, wherein the ostomy barrier assembly is provided with each of the plurality of bladders inflated to provide a generally uniform first compressibility around the convexity, wherein one or more of the plurality of bladders is deflated to adjust the first compressibility to a second compressibility at one or more of corresponding locations to provide a localized and customized adjustment of the compressibility of the convexity, wherein the first compressibility is greater than the second compressibility.

5. The convex ostomy barrier assembly of claim 2, wherein the ostomy barrier assembly is provided with each of the plurality of bladders deflated to provide a generally uniform third compressibility around the convexity, wherein one or more of the plurality of bladders is inflated to adjust the third compressibility to a fourth compressibility at one or more of corresponding locations to provide a localized and customized adjustment of the compressibility of the convexity, wherein the third compressibility is less than the fourth compressibility.

6. The convex ostomy barrier assembly of claim 2, wherein the inflatable bladder is arranged between the convex insert and the skin barrier, wherein each of the plurality of bladders is configured to be inflated or deflated separately to provide a localized and customized adjustment of a slope of the convexity.

7. The convex ostomy barrier assembly of claim 6, wherein the inflatable bladder is arranged in a concave portion of the convex insert.

8. The convex ostomy barrier assembly of claim 6, wherein one or more of the plurality of bladders is inflated to decrease the slope of the convexity at one or more corresponding locations.

9. The convex ostomy barrier assembly of claim 6, wherein one or more of the plurality of bladders is deflated to increase the slope of the convexity at one or more corresponding locations.

10. The convex ostomy barrier assembly of claim 6, wherein the convex ostomy barrier assembly is provided with each of the plurality of bladders filled with air to provide a generally uniform slope around the convexity, wherein one or more of the plurality of bladders can be compressed or popped to increase the slope of the convexity at one or more corresponding locations.

11. The convex ostomy barrier assembly of claim 1, wherein the inflatable bladder is arranged between the convex insert and the skin barrier in a dome area and configured to adjust a depth of the convexity.

12. The convex ostomy barrier assembly of claim 11, wherein the convex barrier assembly is provided with the inflatable bladder substantially deflated to provide a first depth, wherein the inflatable bladder is configured to be inflated by a user to increase the depth to a second depth, wherein the second depth is greater than the first depth.

13. The convex ostomy barrier assembly of claim 11, wherein the convex barrier assembly is provided with the inflatable bladder inflated to provide a third depth, wherein the inflatable bladder is configured to be deflated by a user to decrease the depth to a fourth depth, wherein the fourth depth is less than the third depth.

14. The convex ostomy barrier assembly of claim 1, wherein the inflatable bladder is arranged between the convex insert and the skin barrier in a concave portion of the convex insert and configured to adjust a slope of the convexity.

15. The convex ostomy barrier assembly of claim 14, wherein the convex barrier assembly is provided with the inflatable bladder substantially deflated to provide a first slope, wherein the inflatable bladder is configured to be inflated by a user to decrease the slope to a second slope, wherein the second slope is less than the first slope.

16. The convex ostomy barrier assembly of claim 14, wherein the convex barrier assembly is provided with the inflatable bladder inflated to provide a third slope, wherein the inflatable bladder is configured to be deflated by a user to increase the slope to a fourth slope, wherein the fourth slope is greater than the third slope.

17. The convex ostomy barrier assembly of claim 1, wherein the inflatable bladder is arranged adjacent a distal surface of the convex insert and configured to adjust a compressibility of the convexity.

18. The convex ostomy barrier assembly of claim 17, wherein the convex ostomy barrier assembly is configured such that the compressibility of the convexity can be adjusted by inflating or deflating the inflatable bladder while a depth and a slope of the convexity defined by the convex insert remain unchanged.

19. The convex ostomy barrier assembly of claim 17, wherein the inflatable bladder is arranged proximate a base area of the convex insert.

20. The convex ostomy barrier assembly of claim 17, 17 19, wherein the inflatable bladder is configured to be inflated to increase the compressibility of the convexity and deflated to decrease the compressibility of the convexity.

21. The convex ostomy barrier assembly of claim 1, wherein the convex ostomy barrier assembly includes a fluid inlet and a fluid path connecting the fluid inlet to the inflatable bladder, wherein the fluid inlet and the fluid path provides a path for a fluid to enter or exit the inflatable bladder.

22. The convex ostomy barrier assembly of claim 1, wherein the inflatable bladder is configured to be inflated by inserting a fluid into the inflatable bladder, and wherein the inflatable bladder is configured to be deflated by releasing the fluid from the inflatable bladder.

23. The convex ostomy barrier assembly of claim 21, wherein the fluid is air.

\* \* \* \* \*